United States Patent [19]
Tilley

[11] Patent Number: 5,804,368
[45] Date of Patent: Sep. 8, 1998

[54] METHOD FOR SCREENING FOR PROSTATE CANCER BY MEASURING APOLIPOPROTEIN D LEVELS IN BODY FLUID

[75] Inventor: Wayne Tilley, Bedford, Australia

[73] Assignee: Signet Laboratories, Dedham, Mass.

[21] Appl. No.: 713,790

[22] Filed: Sep. 13, 1996

Related U.S. Application Data

[60] Provisional application No. 60/003874 Sep. 15, 1995.
[51] Int. Cl.$^6$ .............................. C12Q 1/00; C12Q 1/26; G01N 33/53; G01N 33/92
[52] U.S. Cl. .............................. 435/4; 435/7.23; 435/25; 435/34; 435/7.8; 435/7.1; 436/71; 436/74; 436/803; 436/813; 436/811; 436/815

[58] Field of Search .................................. 435/4, 7.23, 25, 435/34, 7.8, 7.1; 436/71, 813, 803, 63, 74, 811, 815

[56] References Cited

PUBLICATIONS

Aspinall et al; J. of Urology; vol. 154, pp. 622–628, Aug. 1995.
McConathy et al; Biochem.; vol. 15, No. 3, pp. 515–520, 1976.

*Primary Examiner*—Louise N. Leary
*Attorney, Agent, or Firm*—Felfe & Lynch

[57] ABSTRACT

The invention is directed to a method for screening for possible prostate cancer presence. The method calls for assaying apolipoprotein D ("ApoD") levels in body fluids, such as serum. Assays for ApoD can be used prognostically, as well as diagnostically.

4 Claims, No Drawings

METHOD FOR SCREENING FOR PROSTATE CANCER BY MEASURING APOLIPOPROTEIN D LEVELS IN BODY FLUID

This application claims priority of provisional application Ser. No. 60/003,874, filed Sep. 15, 1995.

FIELD OF THE INVENTION

This invention relates to methods for determining possibility of prostate cancer in a subject. More particularly, it relates to a screening methodology, whereby a body fluid sample of a subject is tested to assay levels of Apolipoprotein D ("ApoD"), wherein elevated levels of ApoD are indicative of possible prostate cancer in said subject.

BACKGROUND AND PRIOR ART

Apolipoproteins are small protein molecules which are found, in, in complex, micelle structures which also contain phospholipids and neutral lipids. See, e.g., Burtis and Ashwood, ed., *Tietz Textbook of Clinical Chemistry*, (2nd ed, 1994), pages 1019–1058, incorporated by reference.

Apolipoprotein D, or "Apo D", is one of the Apolipoproteins. According to the Tietz textbook at 1023, "virtually nothing is known of ApoD synthesis or catabolism." Indeed, in the materials provided by the Tietz reference relative to various lypoproteinemias, nothing is provided regarding ApoD.

Balbin et al., J. Biochem 271:803–807 (1990), determined that a material referred to as "gross cystic disease fluid" is identical to ApoD. The molecule is found at high concentrations (10–50 mg/ml), in gross cystic disease fluid, especially in such fluid of the breasts of women with gross cystic disease. The reason for its presence is not known.

The gene for ApoD was isolated, cloned and expressed by Drayna, et al, J. Biol. Chem 261:16535–16539 (1986). Comparison to other apolipoproteins shows no homology to these, although there is considerable homology to plasma retinol binding protein.

ApoD expression is stimulated by androgens and interleukin -1, but is downregulated by estrogen. It has also been found that the quantity of cystosolic ApoD, measured in tumors of patients with breast cancer, showed statistically significant correlation with cancer patients who have node positive disease, and thus a poor prognosis.

Mazoujian, et al, Ann NY Acad Sci, 586:188–197 (1990), incorporated by reference, have carried out immunohistochemical studies which showed the presence of ApoD in cancer tissues, such as endothelium, ovary, and prostate tissues. No comparison was made to normal tissues, and no correlation was, or could be drawn, vis a vis ApoD.

Aspinall and Tilley, et al., J. Urol 154:622–628 (1995) incorporated by reference in its entirety, showed a significant increase in expression of ApoD in malignant prostate tissue, as compared to normal, age matched controls.

It is well known that prostate cancer is a cause for concern especially among men over the age of 40. Its occurrence is increasing, and there is a continuing need for diagnostic and screening methods for identifying the condition as early as possible. There is also a continuing need for diagnostic reagents which can accomplish this.

Prostate Specific Antigen ("PSA") is a standard "marker" for prostate cancer. Qualitative and quantitative determination of PSA have achieved diagnostic significance in the area of oncological diagnostics. At present, serological determination of PSA is currently the only accepted, non-invasive method for determining early signs of prostate cancer.

The measurement of PSA, however, is limited in usefulness because while it is diagnostic, it is not prognostic. Thus, there is a need for a method which augments and improves the art by presenting both prognostic and diagnostic assays for prostate cancer.

It has now been found surprisingly, that ApoD serves as a screening "marker" for prostate cancer. It is this observation which is the crux of the invention, elaborated upon in the disclosure which follows.

DETAILED DESCRIPTION OF PREFERRED EMBODIMENTS

EXAMPLE 1

Serum samples were taken from a cohort of male subjects, at Flenders Medical Center, Bedford. Park, South Australia. Serum PSA levels were determined using a commercially available sandwich immunoassay for PSA (Hybritech Tandem™ kit; also see U.S. Pat. No. 4,376,110, incorporated by reference). Once the PSA levels were determined, the samples were divided into 3 groups. The first group contained all samples with levels of PSA less than 4 ng/ml. The second group contained all samples where the levels ran from 4 ng/ml to 10 ng/ml. The third group contained all samples above 10 ng/ml. These groups represent, respectively, normal, borderline/equivocal, and definite prostate cancer levels.

These samples were then tested for ApoD in a solid phase, sandwich ELISA for ApoD, developed by Signet Laboratories. Previously, Albers, et al., Atherosclerosis 39:395–409 (1981), had determined that the average serum concentration of ApoD is 55 $\mu$g/ml.

All serum samples were diluted, generally 3000 fold or more, with assay buffer, to bring ApoD concentrations into the range of the standard assay curve, i.e., 5.0–80 $\mu$g/ml. Assays were carried out in accordance with manufacturer's instructions.

A correction was used to account for dilution, and the result are presented in Table 1 which follows:

TABLE 1

Serum Apolipoprotein D Concentrations in Serum with Known PSA Concentrations

| Group 1 ([PSA] < 4 ng/mL) | Group 2 ([PSA] > 4 and < 10 ng.mL) | Group 3 ([PSA] > 10 ng/ml |
|---|---|---|
| 54.8 | 181.9 | 103.5 |
| 48.6 | 180.9 | 43.1 |
| 58.0 | 57.2 | 106.3 |
| 76.6 | 98.3 | 103.5 |
| 42.0 | 119.7 | 196.5 |
| 78.4 | 126.1 | 67.2 |
| 58.0 | 250.9 | 55.3 |
| 167.6 | 132.8 | 153.1 |
| 137.3 | 200 | 158.0 |
| 71.7 | 187.9 | 108.1 |
| 103.9 | 95.1 | 301.4 |
| 67.7 | 121.1 | 141.6 |
| 74.0 | 60.5 | 199.2 |
| 31.9 | 152.3 | 135.7 |
| 186.5 | 174.9 | 197.1 |
| 120.1 | 177 | 92.3 |
| 20.9 | | 154.1 |
| 72.6 | | 97.1 |
| 69.5 | | 94.7 |
| 48.8 | | 145.0 |
| 0.2 | | 124.4 |
| 70.2 | | 232.3 |

TABLE 1-continued

Serum Apolipoprotein D Concentrations in Serum with
Known PSA Concentrations

| Group 1 ([PSA] < 4 ng/mL) | Group 2 ([PSA] > 4 and < 10 ng.mL) | Group 3 ([PSA] > 10 ng/ml) |
|---|---|---|
| 101.3 | | |
| 50.1 | | |
| 37.4 | | |
| 109.7 | | |
| 89.1 | | |
| 57.3 | | |
| 26.3 | | |
| 86.5 | | |
| 88.1 | | |
| 63.0 | | |
| 54.8 | | |
| 81.6 | | |
| 41.3 | | |
| 103.2 | | |
| 84.7 | | |
| 43.4 | | |
| 62.5 | | |
| 89.0 | | |
| 84.6 | | |
| 82.7 | | |
| 87.0 | | |
| 90.7 | | |
| 80.6 | | |
| 167.3 | | |
| 123.5 | | |
| 61.9 | | |
| 24.2 | | |
| 207.0 | | |
| 103.4 | | |
| 125.8 | | |
| 151.8 | | |
| 49.3 | | |
| 24.0 | | |
| 85.1 | | |
| 120.0 | | |
| 87.6 | | |
| 100 | | |
| 151.4 | | |
| 87.5 | | |
| 115.4 | | |
| 66.3 | | |
| 85.0 | | |
| 123.6 | | |
| 70.5 | | |
| 117.0 | | |
| 71.1 | | |
| 74.6 | | |
| 88.8 | | |
| 14.8 | | |
| 114.7 | | |
| 110.6 | | |
| 216.3 | | |
| 102.7 | | |
| 77.5 | | |
| 162.3 | | |
| 124.1 | | |
| 182.0 | | |
| 97.6 | | |
| 146.2 | | |
| 127.9 | | |
| 24.4 | | |
| 108.0 | | |
| 127.7 | | |
| 49.2 | | |

EXAMPLE 2

Once the data in Table 1 were obtained, statistical analyses was carried out, using Students t-test (two sample), to determine significance of difference in the groups. Analysis follows, in Tables 2, 3 and 4:

TABLE 2

Statistical Analysis of Difference Between
Group 1 (Normal) and Group 2 (Borderline)

|  | Group 1 | Group 2 |
|---|---|---|
| Mean | 89.2 | 144.7 |
| Variance | 1837.5 | 2715.3 |
| No Observations | 86 | 16 |
| t-statistic | −4.0876 | |
| P (two tail) | 0.00063 | |

TABLE 3

Statistical Analysis of Difference Between
Group 1 (Normal) and Group 3 (Cancer)

|  | Group 1 | Group 3 |
|---|---|---|
| Mean | 89.2 | 136.7 |
| Variance | 1837.7 | 3714.4 |
| No Observations | 86 | 22 |
| t statistic | −3.5227 | |
| P (two tail) | 0.00154 | |

TABLE 4

Statistical Analysis of Difference Between
Group 2 (Borderline) and Group 3 (Cancer)

|  | Group 2 | Group 3 |
|---|---|---|
| Mean | 144.7 | 136.7 |
| Variance | 2715.4 | 3714.4 |
| No Observations | 16 | 22 |
| t statistic | −0.6696 | |
| P (two tail) | 0.6695 | |

Statistical analysis of these groups shows that one can say, with greater than 99% certainty that ApoD levels in patients with possible and probable prostate cancer are higher than those not afflicted.

The foregoing describes a method for screening for possible presence of prostate cancer, wherein levels of ApoD are measured, and compared to normal levels. An increase in ApoD concentration is indicative of possible prostate cancer in a subject. Once can follow or precede the ApoD assay with a PSA assay for confirmance if desired, although this second assay is not required as part of the invention.

Body fluid sample as used herein refers to substances such as whole blood, plasma, serum, urine, saliva, and so forth. Blood based samples, such as whole blood, plasma, and most preferably serum, are the samples of choice.

The ApoD can be determined by ELISA, but any form of immunoassay may be used, such as radioimmunoassay, (RIA), an immunofluorescence assay (IFA), and so forth. Also possible are nephelometric, gravitometric, and other homogeneous assays, as are non-immunogenic methods, such as those described by Burtis, et al, supra, at page 1055, Table 13.19, incorporated by reference.

Subject as used herein may refer to any individual believed to be at risk for prostate cancer. As indicated, men over 40 are most susceptible to prostate cancer, although it is believed to be clear that cancer follows no "rules" of affliction, and thus subject refers to any human or animal subject in need of such as assay.

As indicated, supra, an ApoD assay is prognostic for prostate cancer, because normal levels of ApoD are observable using standard methodologies. Thus, one can monitor a subject for increases, or decreases, in ApoD levels so as to determine increased risk of prostate cancer, or perhaps remission following drug therapy, e.g., in contrast, PSA assays do not enable such monitoring.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A method for screening for possibility of prostate cancer in a subject, comprising:

a) determining a level of apolipoprotein D in a body fluid sample of said subject; and
   b) comparing said level of apolipoprotein D obtained in step (a) with a normal level of apolipoprotein D; wherein an elevated level of said apolipoprotein D compared with said normal level of said apolipoprotein D in said body fluid sample is indicative of possible prostate cancer in said subject.

2. The method of claim 1, wherein said body fluid sample is serum.

3. The method of claim 1, comprising determining said level of apolipoprotein D in said body fluid sample-by an immunoassay.

4. The method of claim 3, wherein said immunoassay is an enzyme linked, immunosorbent assay.

* * * * *

UNITED STATES PATENT AND TRADEMARK OFFICE
CERTIFICATE OF CORRECTION

PATENT NO.    : 5,804,368
DATED         : September 8, 1998
INVENTOR(S)   : Wayne Tilley It is certified that error appears in the above-identified patent and that said Letters Patent is hereby corrected as shown below:

Column 1,
Line 19, after first "in" insert -- vivo --.

Column 3,
Table 1, line 28, change "123.5" to -- 113.5 --.

Signed and Sealed this

Third Day of December, 2002

JAMES E. ROGAN
*Director of the United States Patent and Trademark Office*